(12) United States Patent
Linker, Jr.

(10) Patent No.: US 6,188,784 B1
(45) Date of Patent: Feb. 13, 2001

(54) SPLIT OPTICS ARRANGEMENT FOR VISION INSPECTION/SORTER MODULE

(75) Inventor: Frank V. Linker, Jr., Broomall, PA (US)

(73) Assignee: American Tech Manufacturing, Inc., Glenolden, PA (US)

(*) Notice: Under 35 U.S.C. 154(b), the term of this patent shall be extended for 0 days.

(21) Appl. No.: 09/029,685

(22) PCT Filed: Jul. 10, 1997

(86) PCT No.: PCT/US97/12256
  § 371 Date: Mar. 3, 1998
  § 102(e) Date: Mar. 3, 1998

(87) PCT Pub. No.: WO98/04882
  PCT Pub. Date: Feb. 5, 1998

Related U.S. Application Data

(60) Provisional application No. 60/021,622, filed on Jul. 12, 1996, and provisional application No. 60/046,819, filed on May 2, 1997.

(51) Int. Cl.$^7$ ........................................... G06K 9/00
(52) U.S. Cl. ...................... 382/146; 250/559.34; 348/87; 348/131; 356/237.1
(58) Field of Search .................... 382/145–146; 73/104; 348/126, 87, 92, 94, 95, 131, 135; 359/462, 463; 356/237, 237.1; 250/559.34

(56) References Cited

U.S. PATENT DOCUMENTS

| 4,264,202 | 4/1981 | Gugliotta et al. . |
| 4,553,843 | 11/1985 | Langley et al. . |
| 4,608,494 | 8/1986 | Kobayashi et al. . |
| 4,686,637 | 8/1987 | Linker, Jr. et al. . |
| 4,704,700 | 11/1987 | Linker, Jr. et al. . |
| 4,803,871 | * 2/1989 | Harada et al. ..................... 73/104 |
| 4,845,764 | 7/1989 | Ueda et al. . |
| 4,875,778 | 10/1989 | Luebbe et al. . |
| 4,875,779 | 10/1989 | Luebbe et al. . |
| 5,045,710 | 9/1991 | Linkder, Sr. et al. . |
| 5,146,101 | 9/1992 | Linker, Sr. et al. . |
| 5,212,390 | 5/1993 | Lebeau et al. . |

FOREIGN PATENT DOCUMENTS 7-332940 * 12/1995 (JP) ........................ G01B/11/24

* cited by examiner

*Primary Examiner*—Bhavesh Mehta
(74) *Attorney, Agent, or Firm*—Eugene E. Renz, Jr.

(57) ABSTRACT

The present invention provides method and apparatus for determining lead integrity of IC devices characterized by an inspection arrangement which comprises optical elements for back lighting the leads disposed on either side of a trackway for the travel of the IC device thereon. The optical elements are arranged in such a fashion as to simultaneously produce a sharp backlit silhouette image of the leads protruding from either or both sides of the IC device. In accordance with the invention, means are provided for continuously and automatically feeding IC devices through an inspection station in the apparatus where an illumination source through the optical elements directs an intense light beam so that a sharp silhouette or backlit outline of the leads on both sides of the IC device is simultaneously obtained. A single camera is disposed to face the opposing direction of the illumination and optics to receive the silhouette or backlit outline of the IC device leads, as well as the top surface of the device. Electrical signals responsive to the camera image generate an output signal of lead dimensional characteristics. A computational means compares the output signal of lead dimensional characteristics to predetermined acceptable tolerances. A signal responsive to the computational means determines whether the IC device is accepted, rejected, or shunted to a repair station.

9 Claims, 12 Drawing Sheets

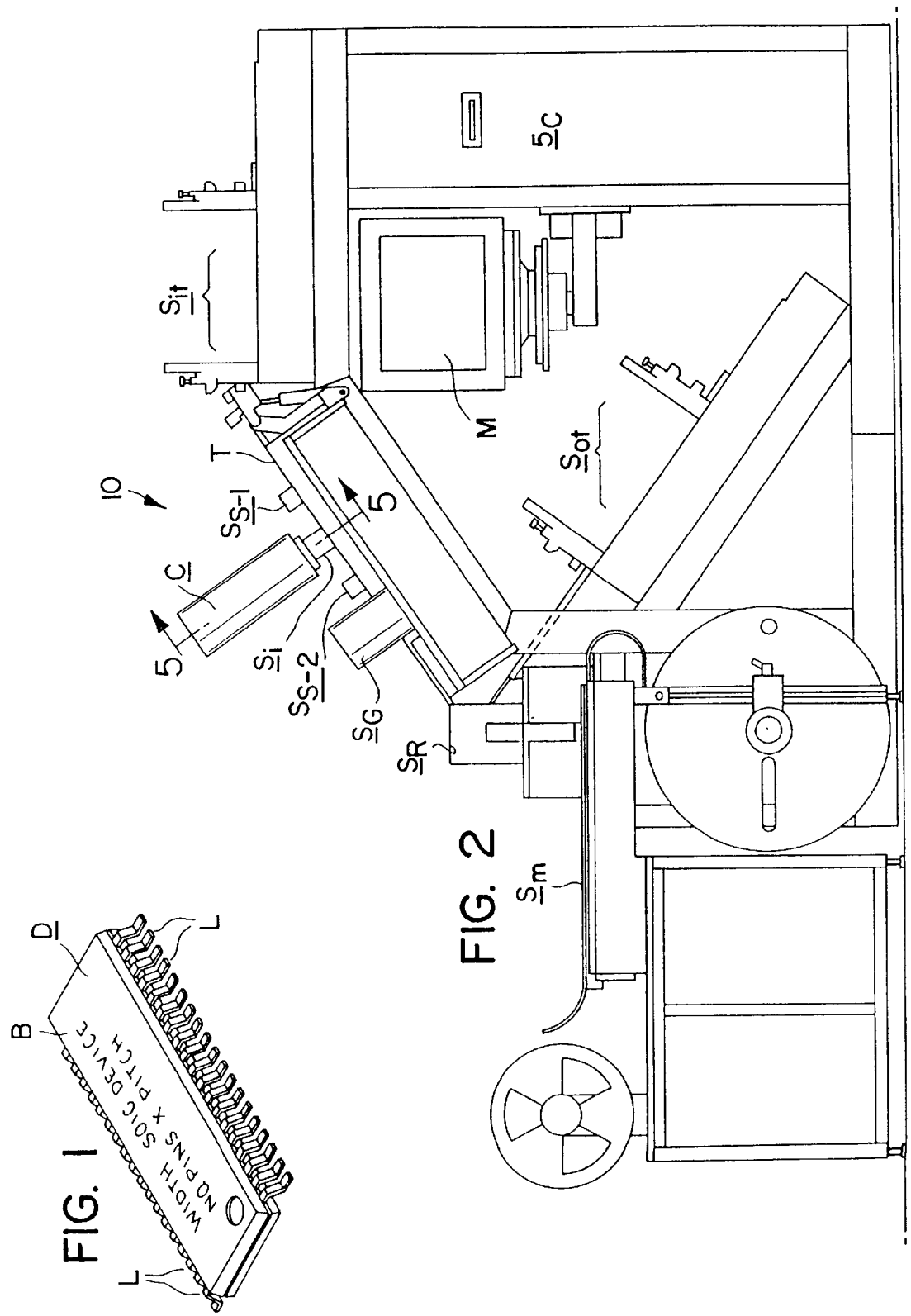

FIG. 4A
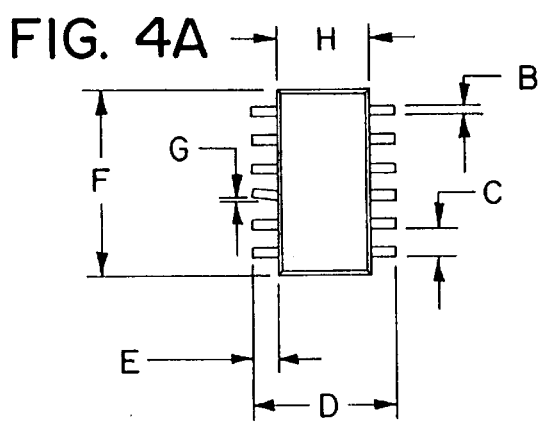
FIG. 4B
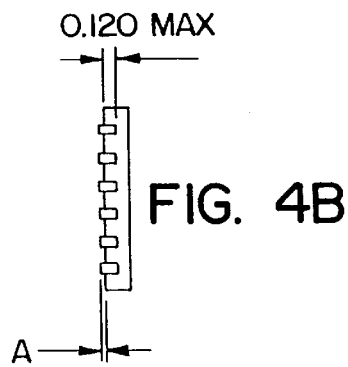
FIG. 4C
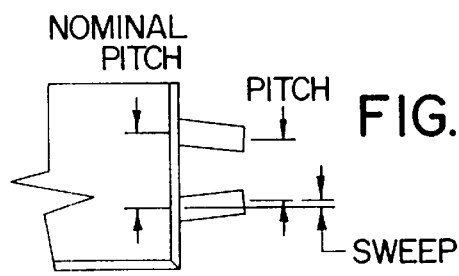
FIG. 4D
| FEATURE | REF | RANGE | ACCURACY | REPEATABILITY |
|---|---|---|---|---|
| STANDOFF HEIGHT | A | 0.000 - 0.030 | 0.0004 | 0.0004 |
| LEAD WIDTH | B | 0.005 - 0.025 | 0.0004 | 0.0004 |
| LEAD PITCH | C | 0.0157 - 0.05 | 0.0004 | 0.0004 |
| LEAD SPREAD | D | 0.230 - 0.700 | 0.0005 | 0.0005 |
| LEAD LENGTH | E | 0.040 - 0.110 | 0.002 | 0.002 |
| PACKAGE LENGTH | F | 0.110 - 0.900 | N/A | N/A |
| LEAD SWEEP +/- | G | 0.000 - 0.020 | 0.0004 | 0.0004 |
| PACKAGE WIDTH | H | 0.150 - 0.600 | N/A | N/A |
| COPLANARITY | I | < 0.030 ERROR | 0.0004 | 0.0004 |
| LEAD COUNT | J | 6 TO 80 PINS | N/A | N/A |

SPLIT OPTICS ARRANGEMENT FOR VISION INSPECTION/SORTER MODULE

RELATED APPLICATIONS

This application claims the benefit of PCT Application PCT/US97/12256 filed Jul. 10, 1997 claiming benefit of U.S. Provisional Applications Nos. 60/046,819 filed May 2, 1997 and 60/021,622 filed Jul. 12, 1996.

TECHNICAL FIELD

The present invention relates to an improved method and apparatus for inspecting lead integrity of electronic components. More specifically, the invention is directed to a novel method and apparatus for determining lead integrity of integrated circuit (IC) components typically used for the assembly of integrated circuits on printed circuit boards (PCB) Such components are comprised of an elongated body portion made of moldable material and have embedded therein a plurality of leads arranged in rows extending from opposite side edges of the body portion and disposed at a perpendicular angular relation thereto. The leads, for appropriate use in a PCB, require lead disposition at a preferred predetermined angle in relation to the body and in substantial mutual relationship one to another and are required to meet standards of uniformity prior to assembly on PCB's. Because of their fragile construction, lead failures are a major cause of electronic equipment failures, and are a major impediment in the automation of electronic devices assembly onto PCB's and other electronic assemblies and frequently cause delays in automated production runs. Consequently, it is necessary to determine the integrity of the leads prior to their attempted mounting. Integrity as used herein includes the determination of whether any of the leads are missing, whether any of the leads have been misaligned with regard to their previous perpendicular relationship with the body of the IC component, and whether leads have changed their mutual parallel relationship.

BACKGROUND ART

The present invention relates to means for vision inspection of dimensional characteristics and sorting out defective IC components, in particular the so-called Surface Mount Devices (hereinafter SMD) typically used for the assembly of integrated circuits on printed circuit boards (PCB), especially those known as "small outline", "very small outline", and "thin small outline". Manufacturers may use thousands of various sizes of SMD devices in automated production runs of electronic equipment. Typical SMD device measurement features and tolerances, as shown in FIGS. 1A, 1B, 1C, and 1D, must be checked and sorted prior to their use. As a response to this need, vision inspection/sorting systems for screening IC devices for lead dimensions against predetermined measurements and tolerances were developed such as that described in several patents owned by the assignee of the present invention and listed in the table below disclosing apparatus and method for determining lead integrity of IC DEVICES, and are incorporated herein by reference in their entirety.

Linker, Jr. APPARATUS AND METHOD FOR LEAD INTEGRITY DETERMINATION FOR SMD DEVICES U.S. Pat. No. 4,686,637 issued Aug. 11, 1987

Linker, Sr. APPARATUS AND METHOD FOR LEAD INTEGRITY DETERMINATION FOR SMD DEVICES U.S. Pat. No. 4,704,700 issued Nov. 3, 1987

Linker, Sr. COPLANARITY INSPECTION MACHINE U.S. Pat. No. 5,045,710 issued Sep. 3, 1991

Linker, Sr. et al. LEAD INSPECTION AND STRAIGHTENING APPARATUS AND METHOD WITH SCANNING U.S. Pat. No. 5,146,101 issued Sep. 8, 1992

In these apparatus, the IC devices are usually gravity fed along an elongated trackway through several stations, and rely on a pin to pin scanning technique to determine IC device lead dimensional and coplanarity integrity. Generally, these apparatus include a first station for lead to lead scanning, a second station for lead coplanarity scanning, a third station for lead to lead straightening, and a fourth station for coplanarity adjustments. Lead to lead and coplanarity checks are performed by a sensor comprising a photodiode, prism, and a photodetector. A scanning means is moved axially along the length of the IC device to provide a signal upon intersection of each lead. Comparison of the signal with a predetermined signal determines the existence and spacing of each lead so that an accept, repair, or reject signal can be generated.

One device presently known for determining lead integrity provides a set of two photosensitive devices aligned one over the other on an axis parallel to the axis of the IC leads which are in proper, substantially parallel mutual relationship. IC leads are caused to intercept a light beam directed at the photosensitive devices by driving IC devices past the photo sensors through the use of motor driven belt arrangement. Thus, as the leads pass in proximity to the photosensitive devices, if the light of one of the photosensitive devices is blocked while the other continues to receive light, there is an indication that the IC lead is bent. The difficulty of such a system is that the motor and belts must be carefully regulated to maintain a constant speed while scanning occurs. Failure to maintain constant speed can result in false deviation determination. Consequently, IC devices that could be used will be rejected and discarded, which indicates the inefficiencies of such prior apparatus A further known type of apparatus for determining the alignment of IC leads on a body is described in U.S. Pat. No. 4,553,843 "Apparatus For Determining the Alignment of Leads On A Body" wherein device leads are made to move axially between a light beam emitter and detector thereby generating signals which provide output data having information of the parallel bending of device leads.

Yet another apparatus described in U.S. Pat. No. 4,264, 202 "Pin Receptacle Inspection Apparatus and Method" uses a collimated light source and a series of mirrors to reflect the light beam off pin receptacles. The reflected light is received by a photodetector which generates an output signal for determining when a predetermined bending threshold has been exceeded. Another apparatus using reflected light for lead inspection is U.S. Pat. No. 5,212,390. In addition to the above patents, apparatus currently commercially marketed by, for instance, Microvision, Texas Instruments, and Q-TEC employ three or four cameras to inspect device leads.

Thus, none of the aforementioned apparatus can inspect all device lead dimensions and characteristics simultaneously and ensure lead integrity in all situations. Further, prior art machines that are dedicated to the specific task of IC device integrity require movable scanning heads or photo emitters and receivers to measure and inspect IC leads. Image based systems such as those cited above, which use multiple cameras, are relatively slow, are costly to implement, and require large capacity computer storage and vision processing power to inspect and check device leads resulting in much slower throughput times and higher overall costs.

Accordingly, it is an object of this invention to provide an inspection means that allows simultaneous checking of IC device lead dimensions, characteristics, and markings with a single imaging means.

Yet another object of this invention is to provide an inspection means that allows inspection of all sizes (body widths and thickness, lead number, lengths, pitch, etc.) of IC devices.

A further object of this invention is to provide an inspection means that significantly increases inspection speed and throughput.

A still further object of this invention is to provide an inspection means that allows continuous feed through of IC devices.

It is another object of this invention to provide an inspection means that allows automatic sorting of defective IC devices without interruption of throughput speed.

DISCLOSURE OF THE INVENTION

The present invention provides method and apparatus for determining lead integrity of IC devices characterized by novel features of construction and arrangement that eliminate some of the problems of prior apparatus discussed above. A principal feature of the present invention resides in an inspection arrangement which comprises optical elements for back lighting the leads disposed on either side of a trackway for the travel of the IC device thereon. The optical elements are arranged in such a fashion as to simultaneously produce a sharp backlit silhouette image of the leads protruding from either or both sides of the IC device. This arrangement, which simultaneously produces a backlit outline of either side is hereinafter referred to as "split optics". In accordance with the invention, means are provided for continuously and automatically feeding IC devices through an inspection station in the apparatus where an illumination source through the split optics directs an intense light beam so that a sharp silhouette or backlit outline of the leads on both sides of the IC device is simultaneously obtained. Photo sensors trigger the illumination source at the precise moment that the IC device is passing the inspection station. A single camera is disposed to face the opposing direction of the illumination and optics to receive the silhouette or backlit outline of the IC device leads, as well as the top surface of the device. Electrical signals responsive to the camera image generate an output signal of lead dimensional characteristics. A computational means compares the output signal of lead dimensional characteristics to predetermined acceptable tolerances. A signal responsive to the computational means determines whether the IC device is accepted, rejected, or shunted to a repair station.

As will be appreciated by one of ordinary skill in the art, the method of the present invention is applicable to devices which have leads on only one side, but the advantage of the split optics pertains to devices which have leads on both sides. This invention, with its unique split optics arrangement, allows a single camera to be used to capture the image, which significantly reduces the time required to compare the image to predetermined measurements and tolerances, thereby allowing for higher inspection speeds and significantly reducing inspection errors.

BRIEF DESCRIPTION OF THE DRAWINGS

For a more complete understanding of the invention, reference is hereby made to the drawings, in which:

These and other objects of the present invention and the various features and details of the operation and construction thereof are hereinafter more fully set forth with reference to the accompanying drawings, where:

FIG. 1 is an isometric view showing one form of semiconductor package that can be inspected by the high speed scanning device of this invention;

FIG. 2 is a schematic side elevational view showing the overall arrangement of a high speed inspection system for inspecting semiconductor packages by means of a single camera and split imaging optical system;

FIG. 4A is a schematic plan view of a semiconductor package showing dimensions measured by the computer in plan view;

FIG. 4B is a schematic side elevational view of the semiconductor package showing dimensions measured by the computer in both side elevational views.

FIG. 4C is an enlarged fragmentary plan view dimensionally defining lead sweep;

FIG. 4D is a table defining the dimensions shown in FIGS. 4A–4C inclusive, the range of the semiconductor packages that can be processed at the inspection station, the accuracy repeatability of the inspected semiconductor packages as they pass through the inspection station;

BEST MODE FOR CARRYING OUT OF THE INVENTION

Figure 3:
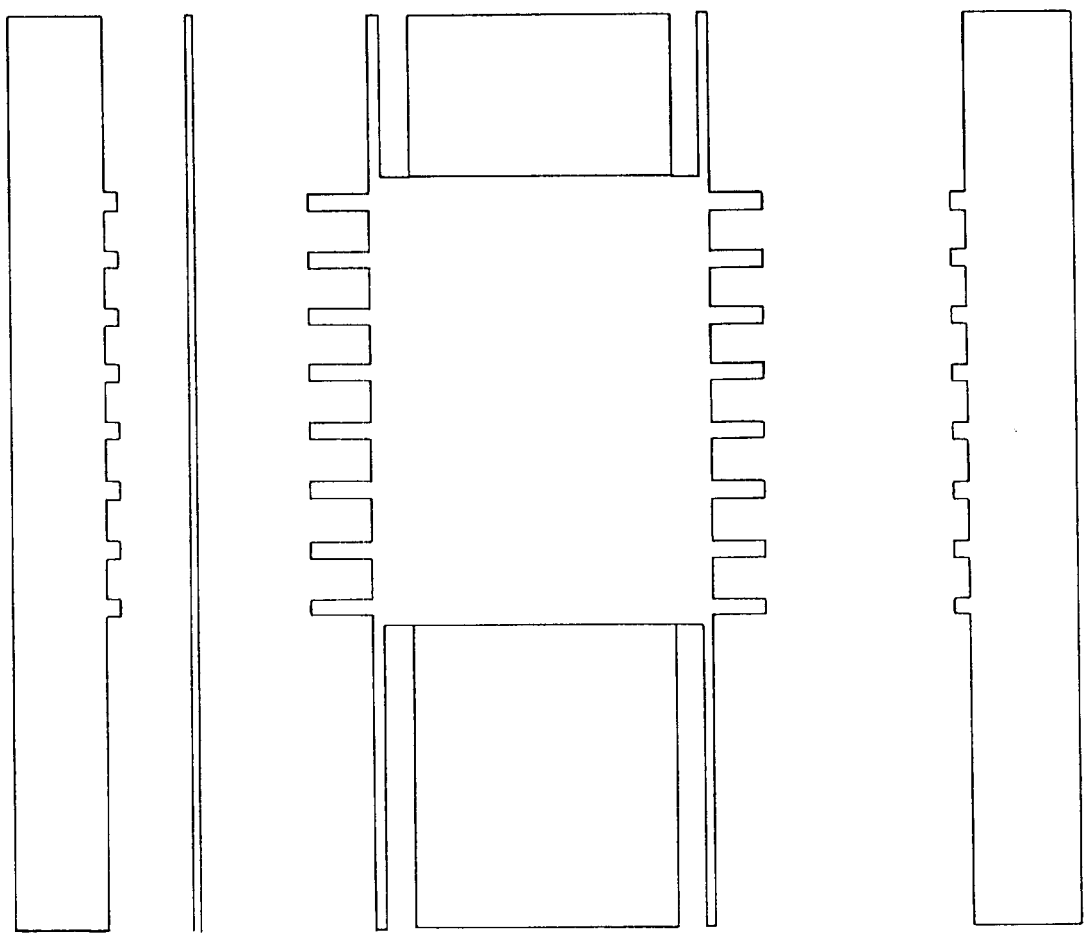
FIG. 3 shows the image taken by the single, charge-coupled-device (CCD) camera of a typical semiconductor package as it moves beneath the high speed, split, imaging optical system at the inspection station.

These and other objects of the present invention and the various features and details of the operation and construction thereof are hereinafter more fully set forth with reference to the accompanying drawings, where:

With reference to the drawings, FIG. 1 illustrates a typical IC device D utilized in the assembly of electronic circuits. The manufacturer of the IC devices normally ships the devices D to the user in either elongated plastic tubes or pockets in tapes on reels. Before the user of the IC devices D can incorporate the IC devices in the automated assembly of electronic circuits, each IC device shipped in either tubes or reels must undergo a lead integrity inspection to insure that all the leads L of the device D make perfect electrical contact when positioned and secured to printed circuit boards by automated equipment. In either the manufacturing of the IC devices D or the shipment and handling of the IC devices, the fragile leads L of the IC devices D can become damaged and will not meet the lead integrity standards required for use in the automated assembly of electronic circuits.

A typical IC device D is shown in FIG. 1 and consist of an elongated body portion B having a series of equally spaced leads L projecting and extending along both lengthwise sides of the body portion B. The leads L have a geometric profile such as a Z shape as shown in FIG. 1 and extend from the mid-point of the body portion B to slightly below the bottom surface of the body B.

FIGS. 4A–4C clearly show the dimensional checks that must be obtained on each IC device D to insure its lead integrity. In order to supply IC devices whose lead integrity has passed inspection onto the automated devices for the assembly of electronic circuits, the accurate inspection of the IC devices must be carried out at very high speed.

To this end and with reference to FIG. 2 of the drawings, there is shown a high speed inspection system generally referred to by reference numeral 10. The high speed inspection system 10 includes a computerized work station 5c, with a monitor M an input tube shuttle station 5it, tracking T, a first singulating station 5-5-1. A high speed inspection station 5, a second singulating station 5-5-2, a high speed gantry sort section 5G, a rotary part transfer station 5A, an outlet tube collection station 5ot and an alternative taping module station 5m.

Tubes filled with IC devices to be inspected are placed in the input tube shuttle Sit and are individually indexed and elevated to align with the inclined trackway T, allowing the IC devices D to slide down the trackway T to a first singulating stations 5-5-1. The singulating station 5-5-1 releases the lead IC device while holding back the remaining stream of IC devices to be tested. The released IC device passes into the high speed inspection stations 5i, the very essence of the invention to be described, where it triggers a strobe light whose light path is designed to back light the IC device from below, directly above the IC device an optical system is designed splitting the silhouetted images of the IC device into both side elevational views with associated leads and a plan view of the leads in addition, the upper surface of the IC device is illuminated to clearly present any data printed on its upper surface. All the above information is instantly presented in one shot to a CCC camera equipped with a telecentric lens mounted directly above the trackway. The images thus created are passed from the CCD camera to a computer which rapidly carries out all the lead checks shown in FIGS. 4A–4D. An actual visual photo of the created split imaging is shown in FIG. 3 of the drawings. This view is typical of what the CCD camera sees.

The inspected IC device continues to move down the trackway until restrained by the second singulating device 5-5-2. The inspected IC device is held long enough for the computer to decide if the inspected IC device is acceptable, repairable or rejected. The inspected IC device is then released to a high-speed gantry sort mechanism station 5G which either places the inspected IC device in a reject tube, lead conditioning tube or allows the IC device to continue on the tracking T to a rotary part transfer mechanism station 5R where the inspected and accepted IC device is directed to either an outlet tube collection stations 5ot or a taping module station Sm though only one taping module is shown another taping module may be included on the opposite side of the system shown.

All of the above station components with the exception of the high-speed single camera split image inspection station are known in the art and require no further description.

The high-speed single camera split image inspection device of the invention will allow the inspection of up to 10,000 IC devices per hour and will now be described in detail with reference to FIGS. 5–11, inclusive.

Figure 5:
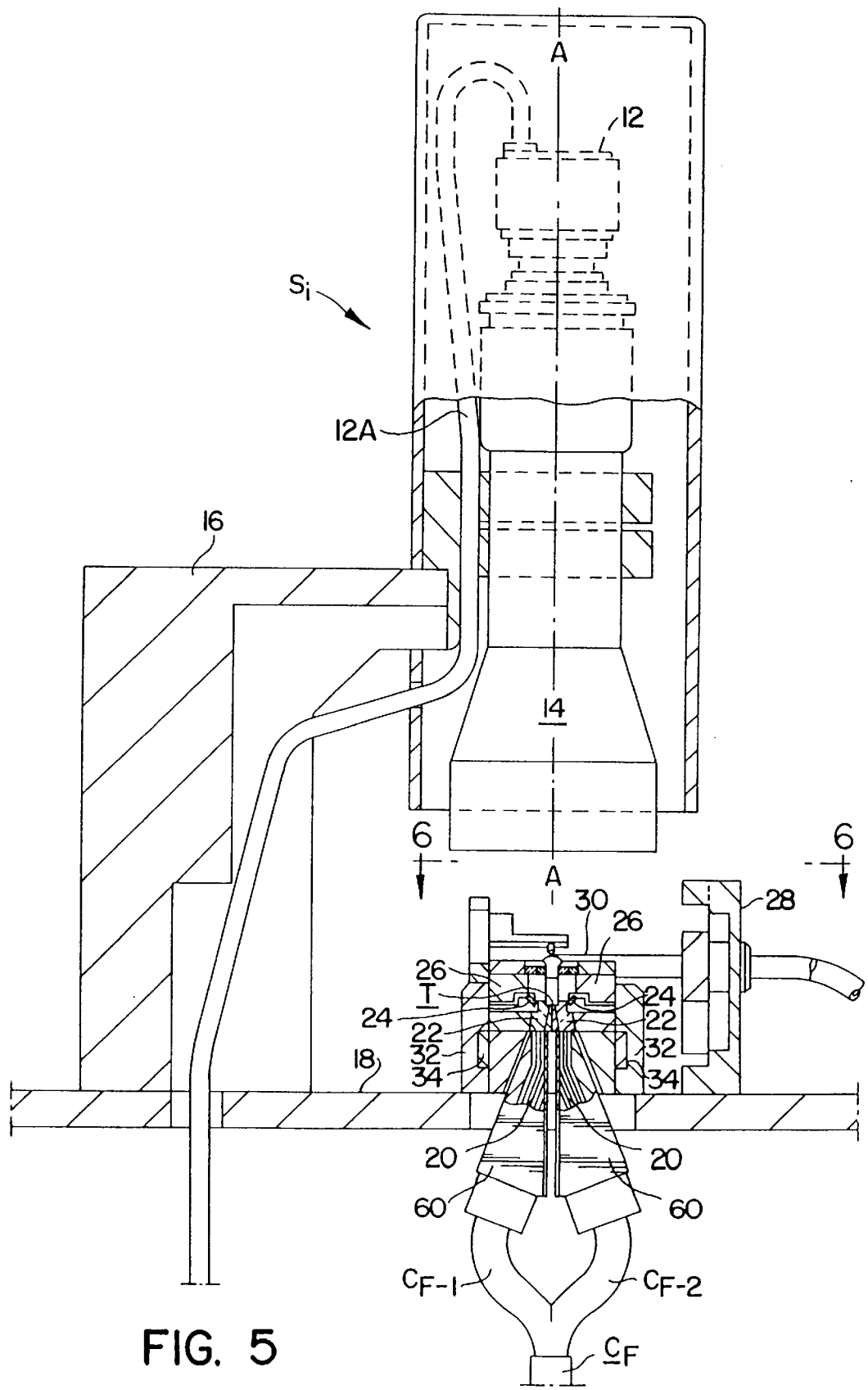
FIG. 5 is an enlarged fragmentary sectional elevational view taken on the lines 5,5 of FIG. 2 showing the overall arrangement of the single camera, and split image optical device of the high speed inspection station.

The general physical arrangement of the elements comprising the high speed, single camera, split image inspection stations 5i are clearly shown in FIG. 5. A CCD camera 12 is interconnected to a computer by means of a cable 12a and the CCD camera 12 is interconnected to a computer by means of a cable 12a and the CCD camera 12 is equipped with a telecentric lens system 14. The camera and associated lens system are supported by means of a pedestal 16 to spacial overlie the centerline of the trackway T with the longitudinal axis A—A of the camera and lens system being normal to the centerline of the trackway T.

The trackway T is adjustably supported on a deck 18 and divided symmetrically about its vertical and longitudinal center lines to allow adjustment for IC devices of different widths. The normal cross sectional shape of the trackway T is modified about the center line A—A of the camera and lens system to accommodate a fiber optic lighting system 20, connected to a first strobe light source not shown, a light diffusion means 22, a side viewing front surfaced mirror system 24 and a height adjustable imaging housing 26 to guard against extraneous light sources. There is also mounted on the deck 18 a bracket system 28 for adjustably positioning a fiber optic lighting means 30 to throw the light from a second strobe light source, not shown, between the imaging housings 26 to illuminate the upper surface of the IC device body B both strobe lights fires simultaneously when triggered by the moving IC device. A pair of rectangular shaped blocks 32 are fixedly mounted to the outer sides of both the left and right hand sides of the trackway T to both retain and guide actuator bars 34 used to position the imaging housings 26 and associated upper guide rails of the trackway so as to accommodate IC devices of greater thickness.

Figure 6:
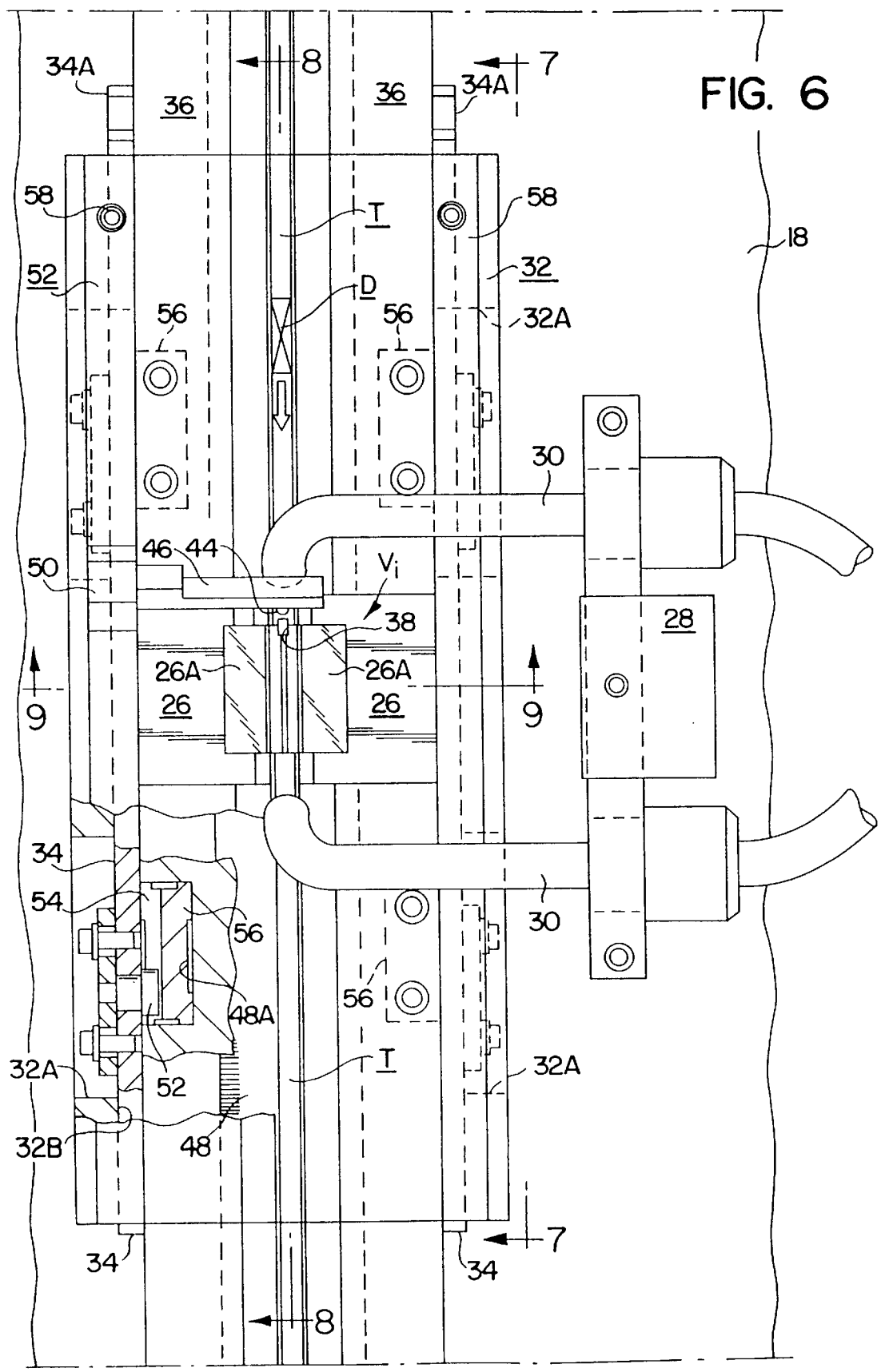
FIG. 6 is an enlarged fragmentary plan view taken on the lines 6,6 of FIG. 5 showing details of the split imaging optical system and tracking.

Now, with reference to FIG. 6 of the drawings, which is an enlarged plan view of the trackway showing the elements of the inspection station device 5i just described in plan view, there is shown then a trackway T bordered on either side by guide rails 36. The guide rails 36 both retain and guide the moving IC device D on the trackway T is a well known manner there is shown in FIG. 6 an IC device D, having been released from the singulating station 5-5-1, approaching the imaging housings 26, both imaging housings include windows 26a which overlie the mirror assemblies 24, the diffuser assemblies 22 and the fiber optic lighting assemblies 20. The windowed areas 26a of the imaging housings 26 now become the target zone in which the moving IC device D and its associated leads L are split imaged in silhouette and viewed by the CCD camera 12 through telecentric lens system 14.

Figure 8:
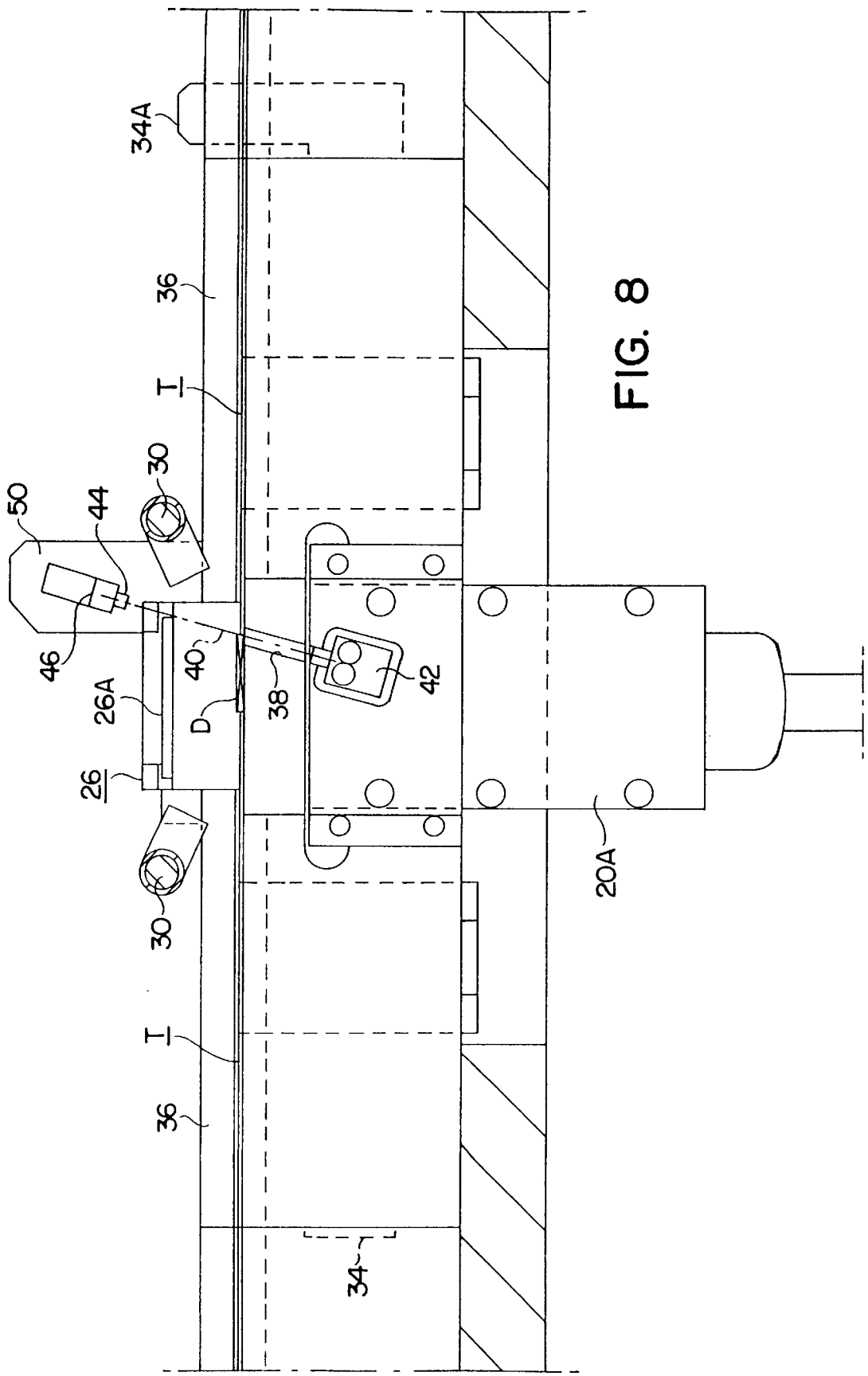
FIG. 8 is an enlarged fragmentary sectional elevational view taken on the lines 8,8 of FIG. 6 showing details of the strobe light ray triggering means.

As the IC device D moves within the imaging housing 26, the IC device passes over a small notched channel 38 formed in the trackway T, see FIG. 8 cutting the beam 40 between an emitter 42 and a detector 44. As the trailing edge of the IC device clears, the notched channel 38 both strobe lights are fired, back lighting the IC device and presenting to the CCD camera 12 a silhouetted split image of the device D as well as a plan view of the IC device D body as described previously and shown in FIG. 3 of the drawings. The detector element 44 is positioned on the inner terminal end of a cantilevered arm 46 and axial aligned with the emitter 42 which is attached to the left hand portion of the trackway body 48. The outer terminal end of the cantilevered arm 46 is attached to bracket 50 that is mounted on the upper surface of the actuator block housing 32 of the left hand portion of the trackway T.

The adjustable bracket system 28 is shown in FIG. 6 supporting and positioning the fiber optic lighting means 30 for illuminating the upper surface of the IC device body B while moving between the imaging housings 26.

Figure 7:
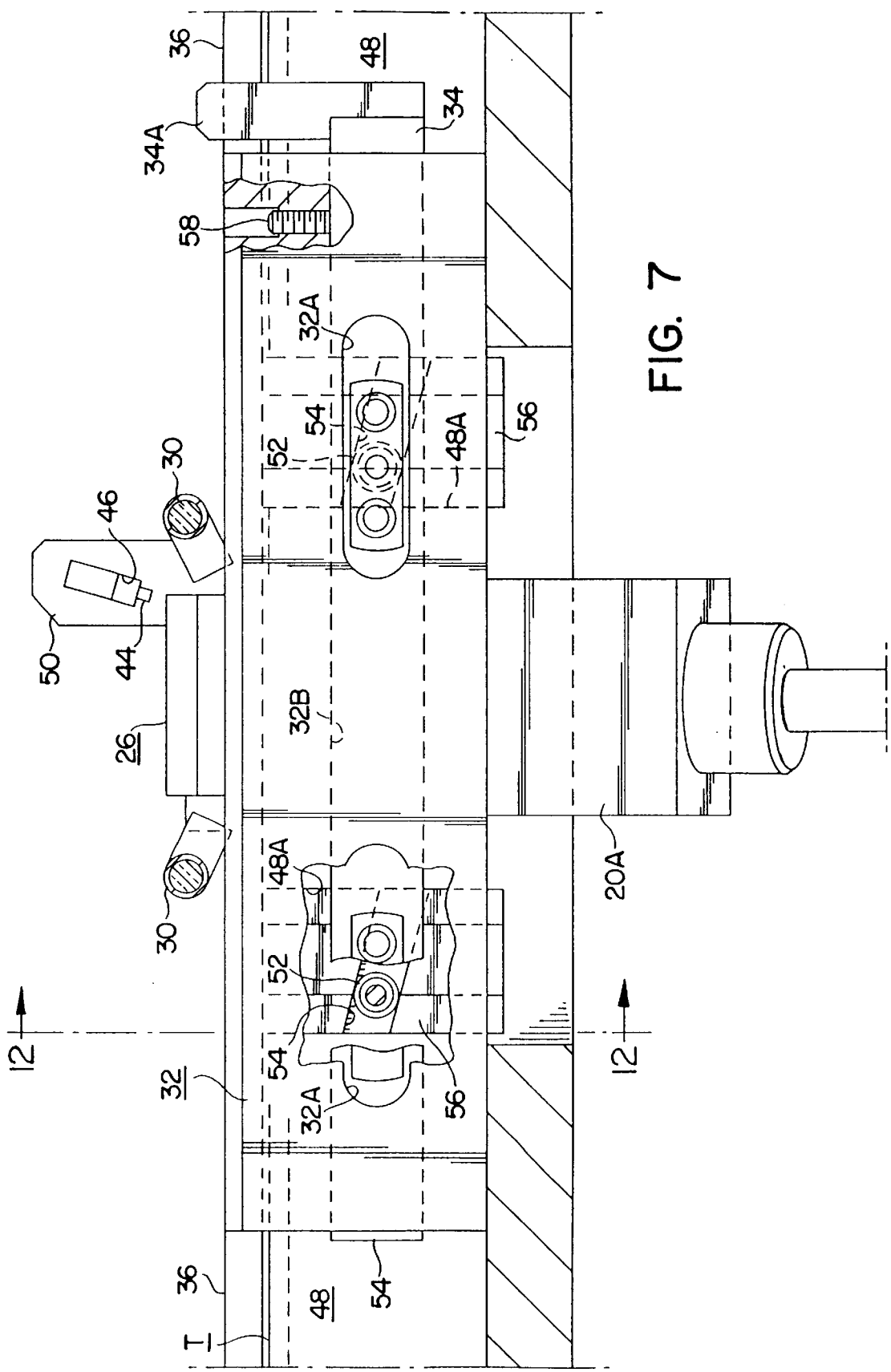
FIG. 7 is an enlarged fragmentary sectional elevational view taken on the lines 7,7 of FIG. 6 showing additional details of the split imaging optical system and tracking.

With reference to both FIGS. 6 and 7 of the drawings, there is shown a height adjustment means for positioning both the upper guide rails 36 and the imaging housings 26 so as to accommodate IC devices of different thickness. The height adjustment means consist of actuator bars 34 slidably retained in the actuator housing blocks 32 and terminating at their up track ends in vertically disposed finger actuation tabs 34A, see FIG. 7. Each actuator block 32 has two spaced generally rectangular shaped, cut-out slots 32A that provide through holes from the outer wall of the actuator housing 32 to the inner slot 32B retaining the actuator bar 34 thereby exposing two spaced portions on the actuator bars 34 for the adjustable mounting of two spaced bearing mounted rollers 52 on each of the actuator bars 34. The rollers 52 interengage with inclined trackway 54 formed in vertically disposed guide post 56, each of the guide blocks 56 are slidably retained recesses 48A formed on the outer sides of each trackway base 48. The upper terminal ends of the guide blocks 56 are secured to the under side of the upper guide rails 36 and associated imaging housing 26.

Thus, it can be shown that by moving the finger tabs 34A in an up track direction, the upper guide rails 36 and associated imaging housing 26 are raised with respect to the trackway T and movement down track of finger tabs 34A. Lower the guide rails 36 and associated imaging housing 26 having positioned the guide rails 36 and associated imaging housing 26, the desired height above the trackway and to allow for the flow of the IC devices D the actuator bars 34 and locked up by means of set screws 58.

Figure 9:
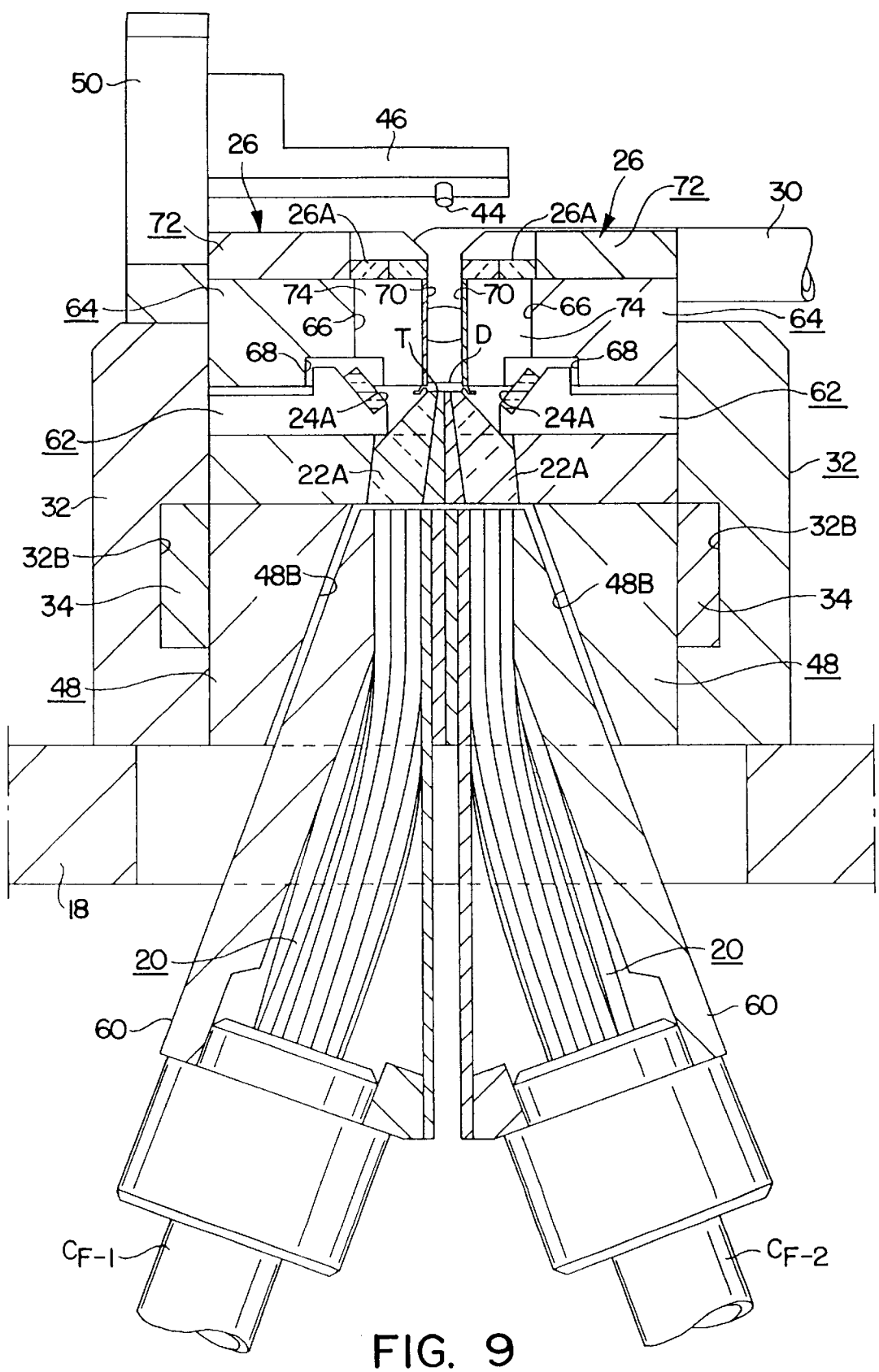
FIG. 9 is a greatly enlarged fragmentary sectional elevational view taken on the lines 9,9 of FIG. 6 showing details of the split imaging optical system and strobe diffused back lighting means.

With reference now to FIG. 9 of the drawings, there is shown an enlarged sectional elevational view showing in greater detail the elements previously described in FIG. 5 that underlie the imaging housing 26. Light triggered in a strobe light source (not shown) is transmitted over a fiber optic cable Cf that is then bifurcated into two distinct cables CF-1 and CF-2, see FIG. 5 of the drawings. The two cables enter and are secured in the lower terminal ends of two cables boxes 60 where short lengths of the fiber optics of each bundle are gathered into a rectangular configuration in plan view. The planar terminal ends of each bundle lie directly beneath the lower surface of two light diffuser prisms 22A. The cable boxes 60 are fixedly retained in pockets 48B of the trackway bases 48. The two diffusion prisms 22A are inset in the bases of two combination diffusion and mirror support frames 62 that are fixedly seated in cut outs formed in the trackway bases 48. The upper planar surface of the diffusion prisms 22A and inner edges of the support frames are sized width wise to conform with the existing trackway width T. The combination diffusion and mirror support frames 62 positionally and angularly support the two front surfaces mirrors 24A with respect to the diffuser prisms 22A and the upper planar surface of the trackway T. The front surfaces mirrors 24A being set to an acute angle with respect to the horizontal of approximately. 52.5 degrees. The imaging housings 26 consist of two rectangular blocks 64 having rectangular shaped openings 66 on their inner trackway facing ends, the blocks 64 also have width wise extending clearance slots 68 on their bottom surface to provide clearance for the mirrors 24A and portions of the mirror support frame 62. The inner trackway facing rectangular shaped openings 66 of the blocks 64 are covered by means of two thin rectangularly shaped metal plates 70 that will slidingly embrace the side edges of an IC device body and whose bottom edges will slidingly clear the upper surfaces of the leads of a moving IC device D forming a continuance of the coextending upper guide rails 36 and in addition creating a imaging that will present light from spilling into the openings 66 when the upper surface of the moving IC device D body is illuminated by the upper fiber optics 30 fixedly attached to the upper surface of the block 64 are window retaining frames 72. The window retaining frames 72 retain the optical nonreflective coated glass viewing windows 26a that cover the rectangular shaped openings 66 of the block 64. The openings 66 in the block 64 now become viewing ports 74 for the CCD camera 12 with the ports 74 isolated from any undesired light source in addition to the above an air stream is introduced along the trackway to keep the mirrored surfaces free from dust particles. It is noted that in this embodiment just described that when the imaging housing assembly 26 is adjusted for height, the mirror system 24a remains fixed.

Figure 10:
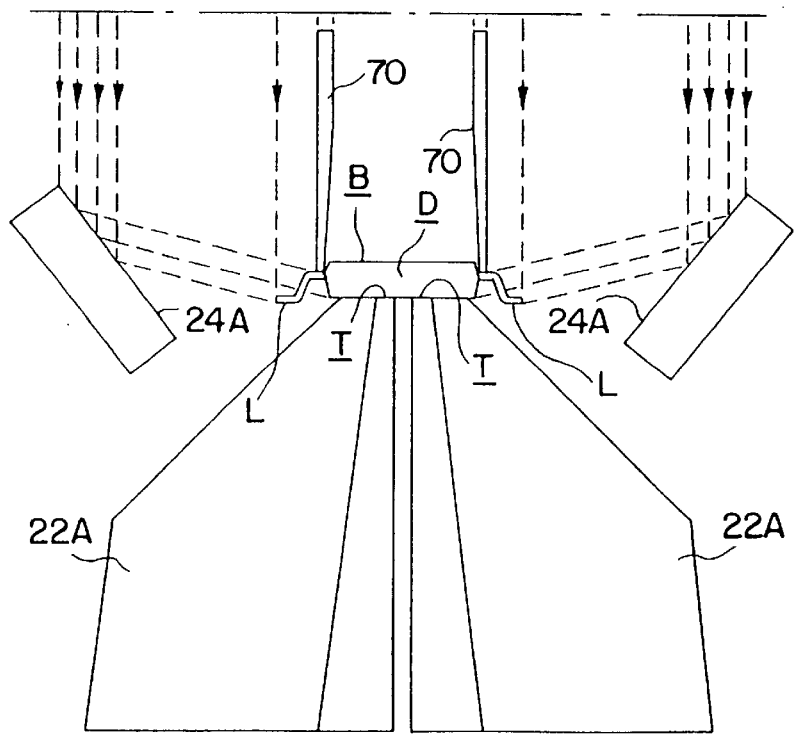
FIG. 10 is a greatly enlarged schematic fragmentary sectional elevational view showing a semiconductor package supported on the light diffuser portions of the trackway positioned midway between two front surface mirrors angularly disposed to the semiconductor package.

FIG. 10 shows IC device D moving down the trackway T between the imaging housings 26. The IC device is slidingly passing between the metal plates 70 and moving along a portion of the tracking formed by the upper surfaces of the diffusion prisms 22a front faced mirrors 24a are positioned to either side of the trackway T and are angularly disposed to the upper plane of the trackway surface by an acute angle of 52.5 degrees.

When the strobe light is triggered, the diffusion prisms 22a are illuminated via the fiber optic bundles and back light the IC device D leads L.

Figure 11:
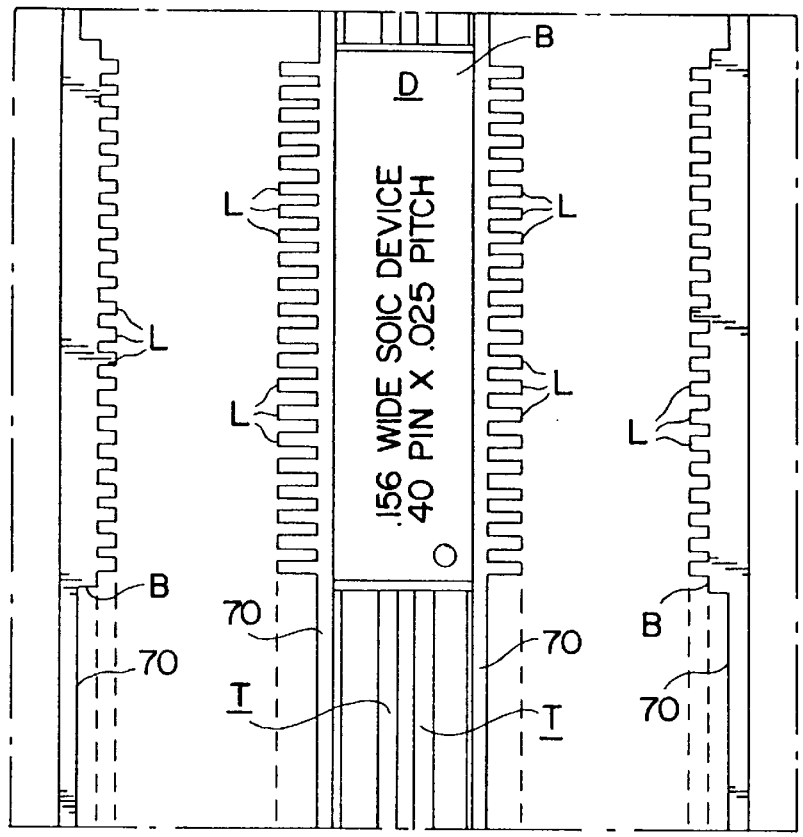
FIG. 11 is an enlarged fragmentary schematic plan view of FIG. 10 showing the instantaneous and simultaneous projection of the silhouette imaging of the semiconductor leads in both plan and side elevations when the strobe light back lights the semiconductor. At the instant of strobe lighting, information carried on the semiconductor upper face is illuminated. All information is presented to the single CCD camera mounted on the telecentric lens system as a single image.

As viewed from above at the instant of illumination, the collective images shown in FIG. 11 are presented to the CCD camera 12. The centrally located image viewed shows the upper surface of the IC device body B with its surface markings and the front and rear edges of the IC device body B. The portion just described is the actual plan view of the IC body illuminated by the upper fiber optic lighting means 30. Adjacent either side of the IC device body in plan there is presented a silhouetted plan view of the IC device leads and the thin plan view of the plates 70. To either side of the central images just described are additional silhouetted images showing partial side elevational views of both sides of the IC device body and its associated leads L along with the lower most edge of the plate 70. All the imaging described above is acquired by the single CCD camera 12 at the instant the IC devices's trailing edge passes notch 38 and beam 40 triggering the strobe lights.

Figure 12A:
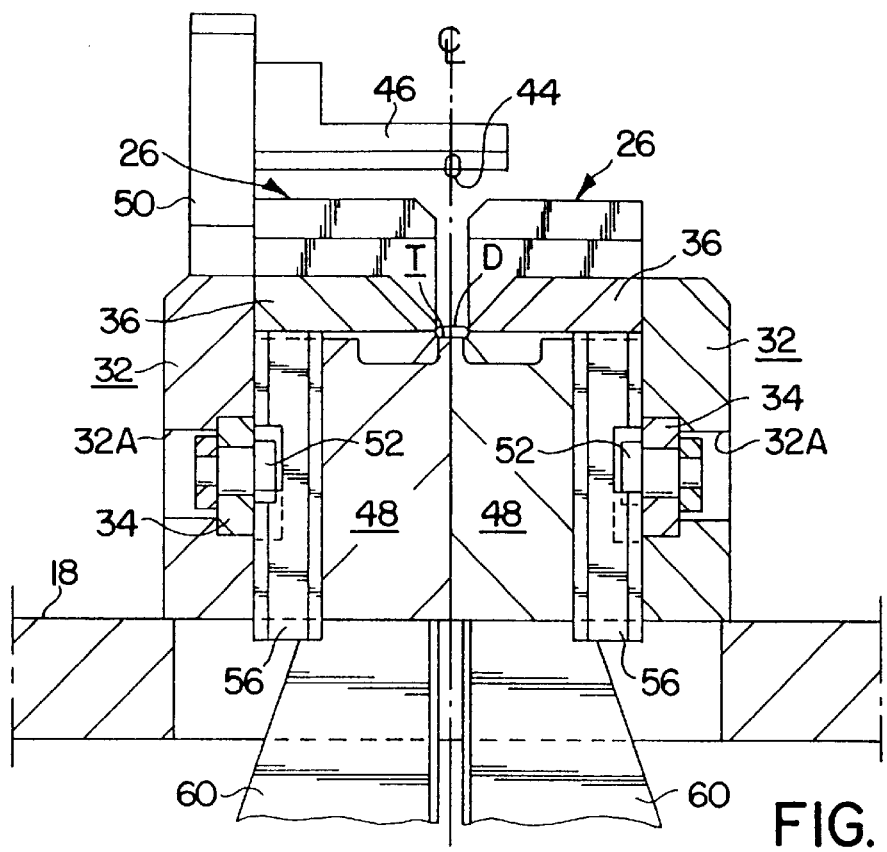
FIG. 12A is a schematic cross sectional view showing the trackway, split imaging optical system and the right and left hand guide rails adjusted to inspect semiconductor packages of the smallest dimensions.
Figure 12B:
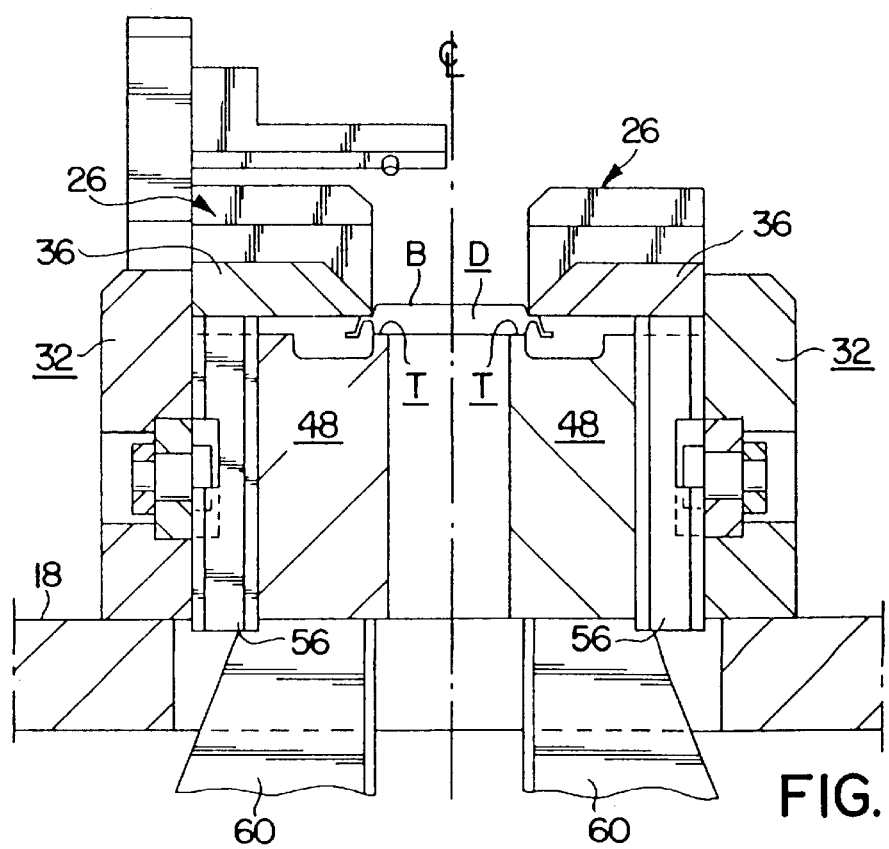
FIG. 12B is a view similar to FIG. 12A, but showing the trackway, split imaging optical system and guide rails adjusted to inspect semiconductor packages of a larger size.

FIG. 12a is a cross-sectional elevational view showing the trackway T and the imaging housing 26 and associated upper guide rails 36 adjusted to inspect IC devices having a body width of 0.150 inches and FIG. 12B is a similar view but showing the trackway T and the imaging housing 26 and associated upper guide rails 36 adjusted to inspect IC devices having a body width of 0.600 inches.

Figure 13:
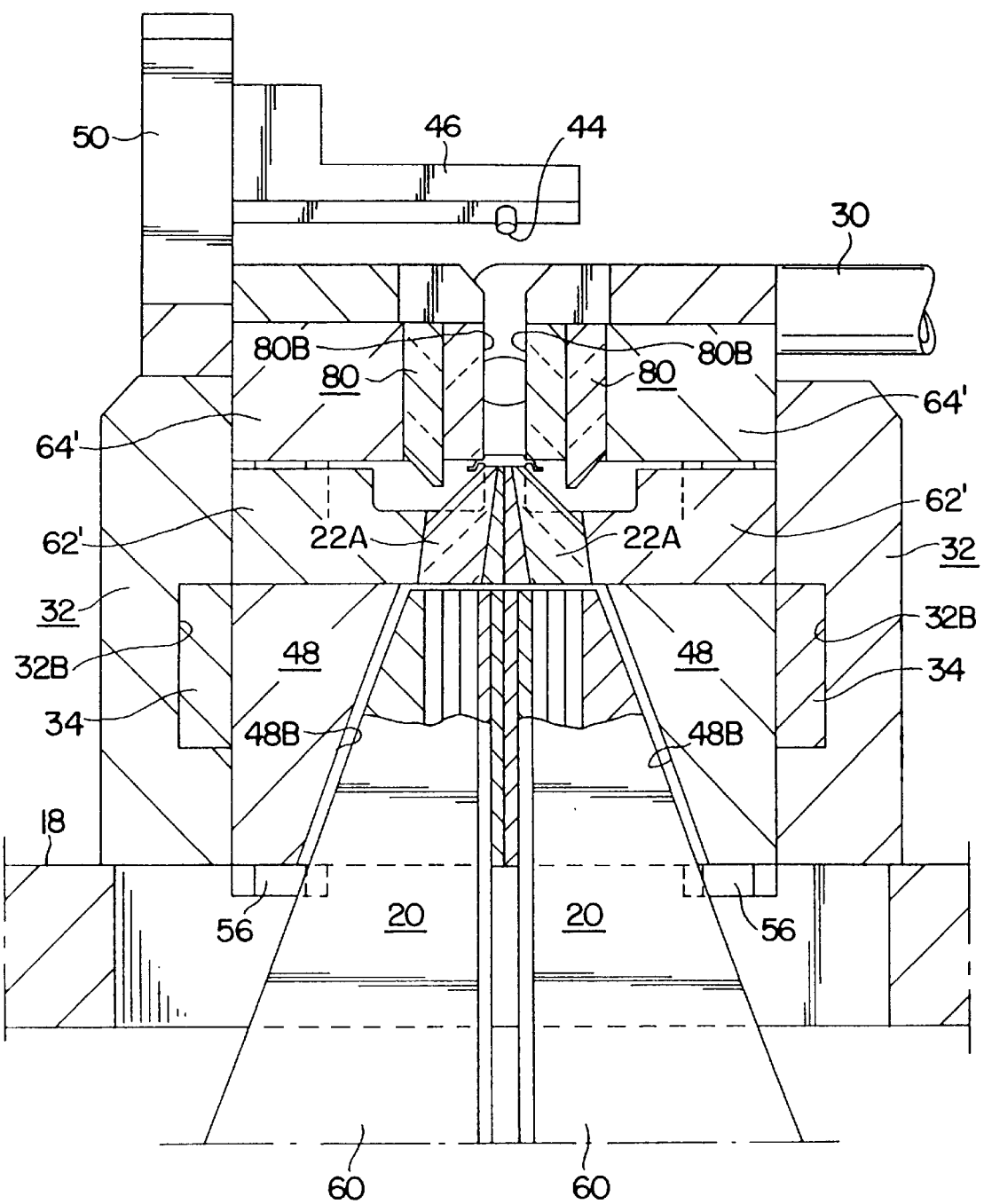
FIG. 13 is a schematic cross sectional view showing a modified optical system of prisms.

FIG. 13 of the drawings is a sectional elevational view similar to FIG. 9 of the drawings but showing a modification of the side viewing mirror assemblies 24 shown in FIG. 7 of the drawings. In FIG. 13 optical prism assemblies 80 replace said mirror assemblies. Certain outer surfaces such as 80b of the prism assemblies 80 are plated to prevent extraneous light from entering the optical systems. The silhouetted split imaging created by the optical prism assemblies is exactly the same as produced by the mirror assemblies 24. The overall assembly is exactly the same as shown in FIG. 9 of the drawings and the parts are given the same reference numbers with the exception of the diffusion and mirrors support frames 62 which have been slightly modified to retain and position only the diffuser prisms 22A and whose upper surfaces are released to accommodate the lower projecting ends of the prism assemblies 80. Therefore, the support frames 62 now become support frames 62' in the same sense the imaging housing blocks 64 are modified so as to retain and position the prism assemblies 80 and given the reference no. 64' in all respects the assembly shown in FIG. 13 functions in the same manner as the assemblies already described in FIGS. 5–12b.

Figure 14:
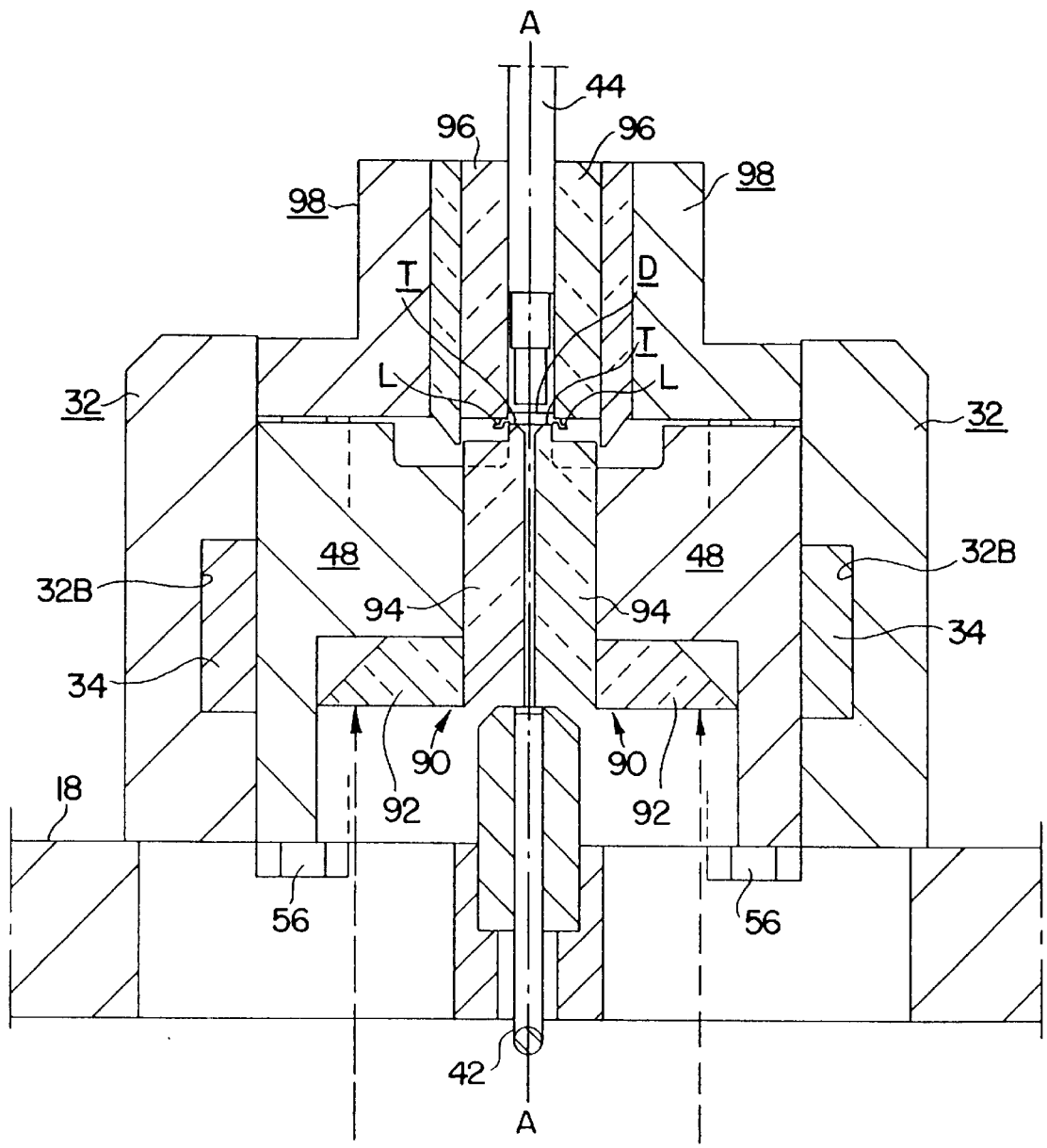
FIG. 14 is a transverse sectional view similar to FIG. 9 showing another modification of the split imaging optical system.

FIG. 14 is a sectional elevational view showing an additional modification for obtaining the collective images shown in FIG. 11 of the drawings but whose assembly differs considerably when compared to FIGS. 9 and 13 of the drawings.

The trackway T is modified about the projected centerline axis A—A of the CCD camera 12 and telecentric lens system 14 to accommodate a below trackway optical system of prisms 90 consisting of horizontally disposed right angle, strobe lighted diffusion prisms 92, abutting vertically disposed right angle light transfer prisms 94 whose upper terminal ends are both sized to conform to the width of the existing trackway t and angled to project the diffused strobe light outwardly at right angles toward the leads L of the IC device D moving along the trackway T. In addition, the upper faces of the prisms 94 have a planar portion to project diffused light vertically upward beneath the leads L of the IC device D. The IC device body B and leads L are now back lighted in the same manner as the embodiments previously described. An above trackway optical system of prisms 96 presents the CCD camera 12 and telecentric lens system 14 with the same collective imaging as shown in FIG. 11 of the drawings. The inner faces, facing the trackway T of the prism system 96 are plated to guard against the strobe fiber optic lighting of the upper surface of the IC device D. The imaging housings 98 containing the above trackway optical system of prisms 96 is adjusted vertically for 16 devices of different thicknesses in the same manner as previously described and the same reference numbers are applied to FIG. 13. The strobe triggering emitter 42 and detector 44 devices have been relocated to lie on the trackway center line and do not move when the trackway T is adjusted widthwise, so that the beam 40 between emitter and detector always lies on the center line of the IC device body B.

As will be appreciated by one of ordinary skill in the art, many modifications and variations of the present invention are possible in light of the above teachings.

What is claimed is:

1. In a method of determining lead integrity of IC devices having leads, comprising the steps of:
   providing illumination of the leads;
   producing a back lit outline of at least one side of the IC device to create a silhouette of the leads;
   simultaneously recording the image of three orthogonal views of the IC device leads with a single camera.

2. The method of claim 1 wherein both sides of said device are backlit simultaneously.

3. The method of claim 1 further comprising the step of recording the image of the top of the device with the single camera.

4. Apparatus for inspecting the leads of an IC device by illuminating the leads and recording the image thereof with a camera, converting the recorded image into an electrical signal and determining the integrity of leads based upon said electrical signal, wherein the improvement comprises:
   means for illuminating said IC devices;
   an optical arrangement operable to simultaneously record images of said IC device in three orthogonal directions;
   means for recording said images with a single camera;
   means for converting said images into electrical signals;
   means for comparing said electrical signals with stored dimensional standards.

5. Apparatus for inspecting the leads of an IC device by illuminating the leads and recording the image thereof with a camera, converting the recorded image into an electrical signal and determining the integrity of leads based upon said electrical signal, wherein the improvement comprises:
   at least one diffusion prism disposed beneath the IC device which creates a backlit image of the leads comprising light transmitted directly to the camera and light reflected by a mirror set at an angle which directs back lit image light from the at least one diffusion prism toward the camera, whereby images of the IC device leads are simultaneously recorded in three orthogonal direction.

6. Apparatus in accordance with claim 1 wherein the prism is laterally adjustable to inspect IC devices of varying widths.

7. Apparatus is claimed in claim 5, including two diffusion prisms disposed beneath the IC device which creates a backlit image of the leads on one side of the device comprising light transmitted directly to the camera and light reflected by two mirrors, each set at an angle which directs back lit image light from the diffusion prisms toward the camera.

8. Apparatus is claimed in claim 5, including at least one optical prism assembly disposed beneath the IC device which creates a backlit image of the leads on one side of the device and which directs the light from the backside of the leads toward the camera.

9. Apparatus is claimed in claim 5, including two optical prism assemblies disposed beneath the IC device, each of which creates a backlit image of the leads on both sides of the device and which direct the light from the backside of the leads toward the camera.

* * * * *